United States Patent
Chidambaram

(10) Patent No.: US 10,182,990 B2
(45) Date of Patent: *Jan. 22, 2019

(54) GASTRIC REFLUX RESISTANT DOSAGE FORMS

(71) Applicant: PATHEON SOFTGELS INC, High Point, NC (US)

(72) Inventor: Nachiappan Chidambaram, Sandy, UT (US)

(73) Assignee: Patheon Softgels Inc., High Point, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/602,700

(22) Filed: May 23, 2017

(65) Prior Publication Data

US 2017/0281555 A1  Oct. 5, 2017

Related U.S. Application Data

(60) Continuation of application No. 12/716,593, filed on Mar. 3, 2010, now Pat. No. 9,693,966, which is a division of application No. 11/316,830, filed on Dec. 22, 2005, now abandoned.

(51) Int. Cl.
| | |
|---|---|
| A61K 9/48 | (2006.01) |
| A61K 9/52 | (2006.01) |
| A61K 35/60 | (2006.01) |
| A61K 47/36 | (2006.01) |
| A61K 47/10 | (2017.01) |
| A61K 47/42 | (2017.01) |

(52) U.S. Cl.
CPC .......... *A61K 9/4825* (2013.01); *A61K 9/4816* (2013.01); *A61K 9/4833* (2013.01); *A61K 35/60* (2013.01); *A61K 47/10* (2013.01); *A61K 47/36* (2013.01); *A61K 47/42* (2013.01)

(58) Field of Classification Search
None
See application file for complete search history.

(56) References Cited

U.S. PATENT DOCUMENTS

| | | |
|---|---|---|
| 4,518,433 A | 5/1985 | Tuason, Jr. |
| 4,719,112 A | 1/1988 | Wittwer |
| 4,816,259 A | 3/1989 | Virgilo |
| 5,146,730 A | 9/1992 | Dietel |
| 5,164,184 A | 11/1992 | Kim |
| 5,264,223 A | 11/1993 | Yamamoto |
| 5,330,759 A | 7/1994 | Stetsko |
| 5,431,917 A | 7/1995 | Abe |
| 5,459,983 A | 10/1995 | Dietel |
| 5,484,598 A | 1/1996 | Morton |
| 5,540,912 A | 7/1996 | Roorda |
| 5,629,003 A | 5/1997 | Hungerbach |
| 6,482,516 B1 | 11/2002 | Dietel |
| 2001/0003647 A1 | 6/2001 | Martin |
| 2001/0024678 A1 | 9/2001 | Xiongwei |
| 2003/0166508 A1 | 9/2003 | Zhang |
| 2003/0175335 A1 | 9/2003 | Xiongwei |
| 2003/0211146 A1 | 11/2003 | Xiongwei |
| 2004/0037877 A1 | 2/2004 | Opheim |
| 2004/0105835 A1 | 6/2004 | Xiongwei |
| 2004/0224020 A1 | 11/2004 | Schoenhard |
| 2004/0265384 A1 | 12/2004 | Xiongwei |

FOREIGN PATENT DOCUMENTS

| | | |
|---|---|---|
| EP | 0888778 A1 | 1/1999 |
| EP | 1072633 A1 | 1/2001 |
| EP | 1132081 A2 | 9/2001 |
| EP | 1447082 A1 | 8/2004 |
| EP | 1518552 A1 | 3/2005 |
| JP | 58172313 A2 | 10/1983 |
| JP | 58194810 A2 | 11/1983 |
| JP | 41027352 A2 | 1/1992 |
| JP | 5245366 A2 | 9/1993 |
| WO | 1999001115 | 1/1999 |
| WO | 2000018835 A1 | 4/2000 |
| WO | 2001070385 A3 | 5/2002 |
| WO | 2003084516 A1 | 10/2003 |
| WO | 2004030658 A1 | 4/2004 |
| WO | 2004050069 A1 | 6/2004 |
| WO | 2009024376 A1 | 2/2009 |

OTHER PUBLICATIONS

Remington, Joseph Price. Remington: the science and practice of pharmacy. 20th Edition Lippincott Williams & Wilkins, 2000. (Year : 2000).*
Allen, et al., "Solid dosage forms and solid modified release drug delivery system", Ansel's Pharmaceutical Dosage forms and Drug Delivery Systems, 81th Edition: 216 (2004).
Demars and Ziegler, "Texture and structure of gelatin/ pectin based gummy confections", food Hydrocolloids, 15:643653 (2001 ).
Joseph and Venkatarm, "Indomethacin sustained release from alginate-gelatin or pectin-gelatin coacervates", 126: 161-168 (1995).
Annonymous, "Gelatin: Pharmaceutical excipients," Handbook of Pharmaceutical Excipients, URL:http://www. medicinescomplete. com/me/expicients/current/100193881.htm?q=gelatin&t=search&ss=text&p=1 #_hit, retrieved Apr. 2, 2014.
Rowe, et al., "Handbook of pharmaceutical excipients, Pecin" , Handbook of 2 Pharmaceutical Expicipents, Pharmaceutical Press, Jan. 1, 2007, pp. 507-508 (2007).
Unknown, Gelling agent & thickening agents—Indokemika group, URL: http://vvww. in dokemika-g rou p .com/products/food_ ingredients/gel ling_ agent_ thick en ing_ agents/index.html, 1 page, retrieved from the Internet Jan. 30, 2014.

* cited by examiner

Primary Examiner — Nissa M Westerberg
(74) Attorney, Agent, or Firm — Brinks Gilson & Lione

(57) ABSTRACT

Gastric resistant film-forming compositions are described herein. The composition contains a gastric resistant natural polymer, a film-forming natural polymer, and optionally a gelling agent. Suitable gastric resistant natural polymers include polysaccharides such as pectin and pectin-like polymers. The film-forming composition can be used to prepare soft or hard shell gelatin capsules which can encapsulate a liquid or semi-solid fill material or a solid tablet (SO-FLET®) containing an active agent and one or more pharmaceutically acceptable excipients. Alternatively, the composition can be administered as a liquid with an active agent dissolved or dispersed in the composition. The compositions are not only gastric resistant but may also prevent gastric reflux associated with odor causing liquids, such as fish oil or garlic oil, encapsulated in a unit dosage form and esophageal irritation due to the reflux of irritant drugs delivered orally.

8 Claims, No Drawings

GASTRIC REFLUX RESISTANT DOSAGE FORMS

CROSS-REFERENCE TO RELATED APPLICATIONS

This application is a continuation of U.S. patent application Ser. No. 12/716,593, filed on Mar. 3, 2010, which is a divisional of U.S. patent application Ser. No. 11/316,830, filed on Dec. 22, 2005, each of which is incorporated herein in its entirety by express reference thereto.

TECHNICAL FIELD

The invention is in the field of gastric resistant dosage forms.

BACKGROUND

The use and manufacture of enteric dosage forms are well known in the art. Such dosage forms are described in Remington's Pharmaceutical Sciences, 18$^{th}$ Ed., Mack Publishing Co., Easton, Pa. (1990). Enteric dosage forms are useful for protecting the contents of the dosage form from the gastric conditions of the stomach and/or to protect gastric tissue from an irritant material contained in the dosage form. Enteric dosage forms can also be useful in preventing gastric reflux due to the presence of odor-causing liquids, such as fish oil or garlic oil, in the dosage form.

Enteric-coated dosage forms are typically produced by a film coating process, where a thin film layer of an acid-insoluble (enteric) polymer is applied to the surface of a pre-manufactured dosage form, such as a tablet, and to a lesser extent hard and soft capsules. The enteric coating method involves spraying an aqueous or organic solution or suspension of one or more enteric polymers onto tumbling or moving tablets or capsules, followed by drying at elevated temperatures. Enteric dosage forms made by this coating method can suffer from various process-related problems that affect the performance and/or appearance of the coating. For example, "orange peel" surface formation, also known as surface roughness or mottling, may result. More seriously, coat integrity failure may occur, such as cracking or flaking of the enteric polymer coating. All coating processes present inherent problems, including possible uneven distribution of the coating ingredients, which can occur under multivariate coating processes.

These problems are common to all enteric dosage forms. However, the problems faced during the coating of gelatin or polysaccharide capsules are even more critical due to the delicate and heat sensitive nature of the soft elastic capsule shell. Both hard and soft capsules can undergo thermally induced agglomeration and distortion of the capsule shell. Moreover, the smoothness and elasticity of the capsule surface makes it difficult to form an intact adhering enteric coating, without a subcoating step to improve the surface of the capsule for coating. Finally, enteric coatings cause the loss of the normally shiny and clear appearance of gelatin capsule shells, which is a major reason for the popularity and acceptance of gelatin capsules.

Attempts to overcome the limitations associated with coated dosage forms have been made. For example, WO 2004/03068 by Banner Pharmacaps, Inc. ("the '068 application") describes a gel mass that is useful in manufacturing enteric soft or hard shell capsules or enteric tablets without the need for a coating. The gel mass contains a film-forming, water-soluble polymer, an acid-insoluble polymer and optionally, one or more excipients such as plasticizers, colorants and flavorants. The '068 application, however, discloses the use of synthetic acid-insoluble polymers such as cellulosic polymers and acrylic acid-methacrylic acid copolymers (EUIDRAGIT®) which are present in a concentration from 8 to 20% by weight of the wet gel mass.

U.S. Patent Application Publication No. 2003/0175335 by Scott et al. ("the '335 application") describes film forming compositions containing pectin, at least one film-forming polymer, and a setting system for preparing soft and hard shell capsules. The concentration of pectin is 5% to 60% by weight, preferably 10% to 40% by weight. The concentration of the film-forming polymer is 40% to 95% by weight, preferably 50% to 85% by weight. The '335 application discloses a film containing 5% to 25%, preferably 10% to 20% by weight pectin which is suitable to prepare hard shell capsules with enteric properties.

There exists a need for a gastric resistant film-forming composition that contains a gastric resistant natural polymer at relatively low concentrations.

Therefore, it is an object of the invention to provide a gastric resistant film-forming composition containing a gastric resistant film-forming composition which contains a gastric resistant natural polymer at relatively low concentrations and methods of manufacturing thereof.

It is further an object of the invention to provide a gastric resistant capsule shell, which can encapsulate a liquid, semi-solid, or solid fill, which contains a gastric resistant natural polymer at relatively low concentrations and methods of manufacturing thereof

SUMMARY

Gastric resistant film-forming compositions containing a gastric resistant natural polymer, a film-forming natural polymer, and optionally a gelling agent are described herein. The compositions can be used for drug delivery either as a liquid or as a gelled capsule. Suitable gastric resistant natural polymers include polysaccharides such as pectin and pectin-like polymers. The concentration of the gastric resistant natural polymer is less than about 5% by weight of the composition, preferably from about 2% to about 4% by weight of the composition. Suitable film-forming natural polymers include gelatin and gelatin-like polymers. The concentration of the film-forming natural polymer is from about 20% to about 40% by weight of the composition, preferably from about 25 to about 40% by weight of the composition. Suitable gelling agents include divalent cations such as $Ca^{2+}$ and $Mg^{2+}$. The concentration of the optional gelling agent is less than about 2% by weight of the composition, preferably less than about 1% by weight of the composition. The composition can further contain one or more plasticizers to facilitate the film-forming process.

The film-forming composition can be used to prepare soft or hard shell gelatin capsules which can encapsulate a liquid or semi-solid fill material or a solid tablet (SOFLET®) containing an active agent and one or more pharmaceutically acceptable excipients. Alternatively, the composition can be administered as a liquid with an active agent dissolved or dispersed in the composition. The compositions are not only gastric resistant but may also prevent gastric reflux associated with odor causing liquids, such as fish oil or garlic oil, encapsulated in a unit dosage form as well as esophageal irritation due to the reflux of irritant drugs delivered orally.

DETAILED DESCRIPTION

Definitions

"Gastric resistant natural polymer," as used herein, refers to natural polymers or mixtures of natural polymers that are insoluble in the acidic pH of the stomach.

"Film-forming natural polymer," as used herein, refers to polymers useful for surface coatings that are applied by spraying, brushing, or various industrial processes, which undergo film formation. In most film-formation processes, a liquid coating of relatively low viscosity is applied to a solid substrate and is cured to a solid, high-molecular-weight, polymer-based adherent film possessing the properties desired by the user. For most common applications, this film has a thickness ranging from 0.5 to 500 micrometers (0.0005 to 0.5 millimeters, or 0.00002 to 0.02 inches).

"Gelling agent," as used herein, refers to substances that undergo a high degree of cross-linking or association when hydrated and dispersed in the dispersing medium, or when dissolved in the dispersing medium. This cross-linking or association of the dispersed phase alters the viscosity of the dispersing medium. The movement of the dispersing medium is restricted by the dispersed phase, and the viscosity is increased.

Composition

Gastric resistant film-forming compositions containing (1) a gastric resistant natural polymer; (2) a film-forming natural polymer; and optionally (3) a gelling agent, are described herein.

Gastric Resistant Natural Polymers

Exemplary gastric resistant natural polymers include, but are not limited to, pectin and pectin-like polymers that typically consist mainly of galacturonic acid and galacturonic acid methyl ester units forming linear polysaccharide chains. Typically, these polysaccharides are rich in galacturonic acid, rhamnose, arabinose, and galactose, for example the polygalacturonans, rhamnogalacturonans and some arabinans, galactans and arabinogalactans. These are normally classified according to the degree of esterification.

In high (methyl) ester ("HM") pectin, a relatively high portion of the carboxyl groups occur as methyl esters, and the remaining carboxylic acid groups are in the form of the free acid or as its ammonium, potassium, calcium or sodium salt. Useful properties may vary with the degree of esterification and with the degree of polymerization. Pectin, in which less than 50% of the carboxyl acid units occur as the methyl ester, is normally referred to as low (methyl) ester or LM-pectin. In general, low ester pectin is obtained from high ester pectin by treatment at mild acidic or alkaline conditions. Amidated pectin is obtained from high ester pectin when ammonia is used in the alkaline deesterification process. In this type of pectin, some of the remaining carboxylic acid groups have been transformed into the acid amide. The useful properties of amidated pectin may vary with the proportion of ester and amide units and with the degree of polymerization.

In one embodiment, the gastric resistant natural polymer is pectin. The gastric resistant natural polymer is present in an amount less than about 5% by weight of the composition, preferably from about 2% to about 4% by weight of the composition.

Film-Forming Natural Polymers

Exemplary film-forming natural polymers include, but are not limited to, gelatin and gelatin-like polymers. In a preferred embodiment, the film-forming natural polymer is gelatin. A number of other gelatin-like polymers are available commercially. The film-forming natural polymer is present in an amount from about 20% to about 40% by weight of the composition, preferably from about 25% to about 40% by weight of the composition.

Gelling Agent

The compositions can optionally contain a gelling agent. Exemplary gelling agents include divalent cations such as $Ca^{2+}$ and $Mg^{3+}$. Sources of these ions include inorganic calcium and magnesium salts and calcium gelatin. The gelling agent is present in an amount less than about 2% by weight of the composition, preferably less than about 1% by weight of the composition.

Plasticizers

One or more plasticizers can be added to the composition to facilitate the film-forming process. Suitable plasticizers include glycerin, sorbitol, sorbitans, maltitol, glycerol, polyethylene glycol, polyalcohols with 3 to 6 carbon atoms, citric acid, citric acid esters, triethyl citrate, and combinations thereof. The concentration of the one or more plasticizers is from about 8% to about 30% by weight of the composition. In one embodiment, the plasticizer is glycerin and/or sorbitol.

Method of Making

The film-forming composition can be used to prepare soft or hard shell gelatin capsules which can encapsulate a liquid or semi-solid fill material or a solid tablet (SOFLET®) containing an active agent and one or more pharmaceutically acceptable excipients. Alternatively, the composition can be administered as a liquid with an active agent dissolved or dispersed in the composition.

Capsules

Shell

The film-forming composition can be used to prepare soft or hard capsules using techniques well known in the art. For example, soft capsules are typically produced using a rotary die encapsulation process. Fill formulations are fed into the encapsulation machine by gravity.

The capsule shell can contain one or more plasticizers selected from the group consisting of glycerin, sorbitol, sorbitans, maltitol, glycerol, polyethylene glycol, polyalcohols with 3 to 6 carbon atoms, citric acid, citric acid esters, triethyl citrate, and combinations thereof.

In addition to the plasticizer(s), the capsule shell can include other suitable shell additives such as opacifiers, colorants, humectants, preservatives, flavorings, and buffering salts and acids.

Opacifiers are used to opacify the capsule shell when the encapsulated active agents are light sensitive. Suitable opacifiers include titanium dioxide, zinc oxide, calcium carbonate, and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes that can cross-link gelatin. As a result, buffering salts and acids can be used in conjunction with flavorings that contain aldehydes in order to inhibit cross-linking of the gelatin.

Fill Material

Agents

Soft or hard capsules can used to deliver a wide variety of pharmaceutically active agents. Suitable agents include analgesics, anti-inflammatory agents, antihelmintics, anti-arrhythmic agents, anti-bacterial agents, anti-viral agents, anti-hypertensive agents, anti-coagulants, anti-depressants, anti-diabetics, anti-epileptics, anti-fungal agents, anti-gout agents, anti-malarials, anti-migraine agents, anti-muscarinic agents, anti-neoplastic agents, erectile dysfunction improvement agents, immunosupressants, anti-protozoal agents, anti-thyroid agents, anxiolytic agents, sedatives, hypnotics, neuroleptics, -blockers, cardiac inotropic agents, corticosteroids, diuretics, anti-parkinsonian agents, gastro-intestinal agents, histamine H1 and H2 receptor antagonists, keratolytics, lipid regulating agents, anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, vitamins, minerals, and mixtures thereof.

Typical fill materials include, but are not limited to, fish oil, garlic oil, soybean oil, peppermint oil, eucalyptus oil, horse chestnut seed extract, valproic acid, proton pump inhibitors, probiotics, and medium chain triglycerides ("MCT").

Excipients

Fill formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to surfactants, humectants, plasticizers, crystallization inhibitors, wetting agents, bulk filling agents, solubilizers, bioavailability enhancers, pH adjusting agents, and combinations thereof.

Solutions and Suspensions

Alternatively, the composition can be administered as a liquid with an active agent dissolved (e.g., solution) or dispersed (e.g., suspension) in the composition. Suitable active agents are described above. The solution or suspension may be prepared using one or more pharmaceutically acceptable excipients. Suitable excipients include, but are not limited to, surfactants, humectants, plasticizers, crystallization inhibitors, wetting agents, bulk filling agents, solubilizers, bioavailability enhancers, pH adjusting agents, flavorants, and combinations thereof.

EXAMPLES

The following film-forming compositions were used to prepare stable soft gelatin capsules using techniques well known in the art.

Example 1. Gastric Resistant Dosage Form

The composition of the gastric resistant dosage form is shown below.

| Component | % by weight of the Composition |
| --- | --- |
| Pectin | 4.04 |
| Water | 70.78 |
| Calcium chloride (CaCl$_2$) | 0.05 |
| Gelatin (150 bloom bovine bone) | 17.70 |
| Glycerin | 7.43 |

Example 2. Gastric Resistant Dosage Form

The composition of the gastric resistant dosage form is shown below.

| Component | % by weight of the composition |
| --- | --- |
| Pectin | 4.04 |
| Water | 70.78 |
| Calcium chloride (CaCl$_2$) | 0.05 |
| Gelatin (175 bloom pig skin) | 17.70 |
| Glycerin | 7.43 |

Example 3. Gastric Resistant Dosage Form

The composition of the gastric resistant dosage form is shown below.

| Component | % by weight of the composition |
| --- | --- |
| Pectin | 4.04 |
| Water | 70.71 |
| Calcium chloride (CaCl$_2$) | 0.05 |
| Gelatin (150 bloom bovine bone) | 17.73 |
| Glycerin | 7.43 |

Example 4. Gastric Resistant Dosage Form

The composition of the gastric dosage form is shown below.

| Component | % by weight of the composition |
| --- | --- |
| Pectin | 4.04 |
| Water | 70.71 |
| Calcium chloride (CaCl$_2$) | 0.03 |
| Gelatin (150 bloom bovine bone) | 17.75 |
| Glycerin | 7.43 |

Example 5. Gastric Resistant Dosage Form

The composition of the gastric dosage form is shown below.

| Component | % by weight of the composition |
| --- | --- |
| Pectin | 4.04 |
| Water | 70.71 |
| Calcium chloride (CaCl$_2$) | 0.01 |
| Gelatin (150 bloom bovine bone) | 17.77 |
| Glycerin | 7.43 |

Example 6. Gastric Resistant Dosage Form

The composition of the gastric dosage form is shown below.

| Component | % by weight of the composition |
|---|---|
| Pectin | 4.04 |
| Water | 70.71 |
| Calcium chloride (CaCl$_2$) | 0.007 |
| Gelatin (150 bloom bovine bone) | 17.77 |
| Glycerin | 7.43 |

Example 7. Gastric Resistant Dosage Form

The composition of the gastric dosage form is shown below.

| Component | % by weight of the composition |
|---|---|
| Pectin | 4.04 |
| Water | 68.99 |
| Calcium chloride (CaCl$_2$) | 0.013 |
| Gelatin (150 bloom bovine bone) | 17.79 |
| Glycerin | 9.17 |

Example 8. Gastric Resistant Dosage Form

The composition of the gastric dosage form is shown below.

| Component | % by weight of the composition |
|---|---|
| Pectin | 4.04 |
| Water | 61.89 |
| Calcium chloride (CaCl$_2$) | 0.013 |
| Gelatin (150 bloom bovine bone) | 22.79 |
| Glycerin | 11.27 |

Example 9. Gastric Resistant Dosage Form

The composition of the gastric dosage form is shown below.

| Component | % by weight of the composition |
|---|---|
| Pectin | 4.04 |
| Water | 54.79 |
| Calcium chloride (CaCl$_2$) | 0.013 |
| Gelatin (150 bloom bovine bone) | 27.79 |
| Glycerin | 13.37 |

Example 10. Gastric Resistant Dosage Form

The composition of the gastric dosage form is shown below.

| Component | % by weight of the composition |
|---|---|
| Pectin | 4.04 |
| Water | 47.69 |
| Calcium chloride (CaCl$_2$) | 0.013 |
| Gelatin (150 bloom bovine bone) | 32.79 |
| Glycerin | 15.47 |

Example 11. Gastric Resistant Dosage Form

The composition of the gastric dosage form is shown below.

| Component | % by weight of the composition |
|---|---|
| Pectin | 2.42 |
| Water | 49.11 |
| Calcium chloride (CaCl$_2$) | 0.004 |
| Gelatin (150 bloom bovine bone) | 33.41 |
| Glycerin | 15.05 |

Example 12. Gastric Resistant Dosage Form

The composition of the gastric dosage form is shown below.

| Component | % by weight of the composition |
|---|---|
| Pectin | 2.42 |
| Water | 49.02 |
| Calcium chloride (CaCl$_2$) | 0.008 |
| Gelatin (150 bloom bovine bone) | 33.60 |
| Glycerin | 15.05 |

Example 13. Gastric Resistant Dosage Form

The composition of the gastric dosage form is shown below.

| Component | % by weight of the composition |
|---|---|
| Pectin | 2.42 |
| Water | 49.11 |
| Calcium chloride (CaCl$_2$) | 0.016 |
| Gelatin (150 bloom bovine bone) | 33.41 |
| Glycerin | 15.05 |

Example 14. Gastric Resistant Dosage Form

The composition of the gastric dosage form is shown below.

| Component | % by weight of the composition |
|---|---|
| Pectin | 2.42 |
| Water | 49.11 |
| Calcium chloride (CaCl$_2$) | 0.031 |
| Gelatin (150 bloom bovine bone) | 33.39 |
| Glycerin | 15.05 |

Example 15. Gastric Resistant Dosage Form

The composition of the gastric dosage form is shown below.

| Component | % by weight of the composition |
| --- | --- |
| Pectin | 2.50 |
| Water | 47.69 |
| Calcium chloride (CaCl$_2$) | 0.0054 |
| Gelatin (150 bloom bovine bone) | 34.33 |
| Glycerin | 15.47 |

Example 16. Gastric Resistant Dosage Form

The composition of the gastric dosage form is shown below.

| Component | % by weight of the composition |
| --- | --- |
| Pectin | 3.03 |
| Water | 49.11 |
| Calcium chloride (CaCl$_2$) | 0.0049 |
| Gelatin (150 bloom bovine bone) | 32.81 |
| Glycerin | 15.05 |

Example 17. Gastric Resistant Dosage Form

The composition of the gastric dosage form is shown below.

| Component | % by weight of the composition |
| --- | --- |
| Pectin | 3.03 |
| Water | 47.68 |
| Calcium chloride (CaCl$_2$) | 0.0065 |
| Gelatin (150 bloom bovine bone) | 33.81 |
| Glycerin | 15.47 |

Example 18. Gastric Resistant Dosage Form

The composition of the gastric dosage form is shown below.

| Component | % by weight of the composition |
| --- | --- |
| Pectin | 3.03 |
| Water | 49.11 |
| Gelatin (150 bloom bovine bone) | 32.81 |
| Glycerin | 15.05 |

Unless defined otherwise, all technical and scientific terms used herein have the same meanings as commonly understood by one of skill in the art to which the disclosed invention belongs.

I claim:

1. A method for manufacturing an oral gastric resistant soft capsule, the method comprising:
   (a) preparing a gel mass composition consisting of: about 25% to about 40% by weight gelatin, about 8% to about 30% by weight of one or more plasticizers, about 2% to about 5% by weight pectin, less than 1% by weight of a gelling agent consisting of calcium salts or magnesium salts, and water;
   (b) casting the gel mass into films or ribbons; and
   (c) forming a gastric resistant soft capsule encapsulating a fill material using rotary die encapsulation.

2. The method of claim 1, wherein the plasticizer consists of one or more of glycerin, sorbitol, sorbitans, maltitol, glycerol, polyethylene glycol, polyalcohols with 3 to 6 carbon atoms, citric acid, citric acid esters, triethyl citrate, or combinations thereof.

3. The method of claim 1, wherein the plasticizer consists of glycerin or sorbitol.

4. The method of claim 1, wherein the gelling agent consists of calcium salts.

5. The method of claim 1, wherein the fill material comprises one or more pharmaceutically active agents or nutritional agents and optionally one or more pharmaceutically acceptable excipients.

6. The method of claim 1, wherein the fill material comprises one or more nutritional oils.

7. A gastric resistant soft capsule dosage form made by the method of claim 5.

8. A gastric resistant soft capsule dosage form comprising one or more nutritional oils made by the method of claim 6.

* * * * *